United States Patent [19]

Swart

[11] Patent Number: 4,865,028

[45] Date of Patent: Sep. 12, 1989

[54] DEVICE FOR CARRYING OUT A THERAPEUTIC TREATMENT BY MEANS OF A REFRIGERANT

[76] Inventor: Wilhelmus J. B. Swart, A. van Gelderweg 1, 5361 Ct Grave, Netherlands

[21] Appl. No.: 201,922

[22] Filed: Jun. 3, 1988

[51] Int. Cl.$^4$ .............................................. A61B 17/36
[52] U.S. Cl. .......................... 128/303.1; 128/DIG. 27
[58] Field of Search ..................... 128/303.1, 388–402, 128/DIG. 27

[56] References Cited

U.S. PATENT DOCUMENTS

| | | | |
|---|---|---|---|
| 3,794,039 | 2/1974 | Kollner et al. | 128/400 |
| 3,901,241 | 8/1975 | Allen | 128/303.1 |
| 3,924,628 | 12/1975 | Droegemueller et al. | 128/303.1 |
| 3,938,898 | 2/1976 | Reitknecht | 401/133 |
| 4,082,096 | 4/1978 | Benson | 128/303.1 |
| 4,116,199 | 9/1978 | Bryne | 128/303.1 |
| 4,367,743 | 1/1983 | Gregory | 128/303.1 |
| 4,377,168 | 3/1983 | Rzusa et al. | 128/303.1 |

FOREIGN PATENT DOCUMENTS

| | | |
|---|---|---|
| 67705 | 8/1973 | Luxembourg . |
| 291694 | 7/1964 | Netherlands . |
| 6612442 | 3/1967 | Netherlands . |
| 1105590 | 3/1968 | United Kingdom . |

Primary Examiner—Max Hindenburg
Attorney, Agent, or Firm—Young & Thompson

[57] ABSTRACT

A method is provided for the therapeutic treatment of a portion of the skin of a human or animal by the freezing of said portion of said skin by application of a refrigerant thereto through an outlet in a discharge end of a supply tube connected to a spray can serving as a source of said refrigerant in the liquid phase, a supply end of said supply tube extending into said liquid phase refrigerant in said spray can, the improvement wherein said refrigerant is applied to said portion of said skin through a cotton wool bud which encompasses said discharge end of said supply tube and which cotton wool bud surrounds said outlet of said supply tube.

4 Claims, 1 Drawing Sheet

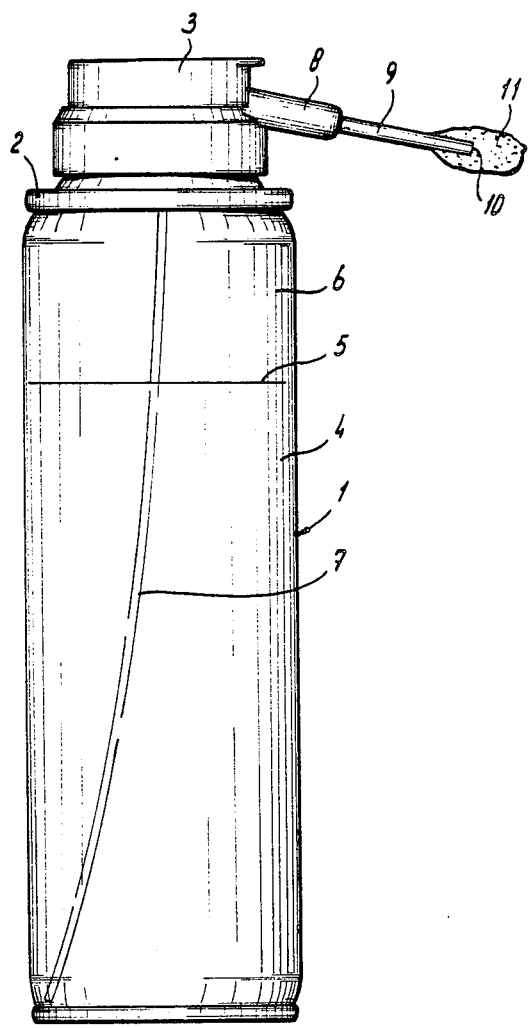

DEVICE FOR CARRYING OUT A THERAPEUTIC TREATMENT BY MEANS OF A REFRIGERANT

The invention relates to a method for carrying out a therapeutic treatment, such as the removal of warts, on a part of the human or animal body by local freezing, the place to be treated being treated by means of a cotton wool bud or similar plug of absorbent material which has been cooled by means of a liquid refrigerant, which is present as liquid in the pressurised container and vaporises in escaping, at a temperature of less than 0° C.

Such a method is known and, to be specific, by making use clinically of liquid nitrogen which has a boiling point of −180° C. The cotton bud is immersed in the liquid nitrogen and then brought into contact with the place to be treated.

This, as it were, classical use of liquid nitrogen is subject to a number of practical drawbacks under clinical conditions. The availability and shelflife of liquid nitrogen is subject to limitations. The liquid nitrogen is made available in special double-walled, thermally insulated containers which are usually available only for a short time, usually only one day, for the treatment of warts. The general practitioner therefore has to arrange a special surgery.

For the effective removal of undesirable tissues, such as warts, it is necessary to destroy the cell structure by freezing within a very short period of time and, in view of its very low boiling point under atmospheric conditions, liquid nitrogen is in fact particularly suitable for this purpose.

The object of the invention is therefore to provide a method and device which offers a number of advantages over the known method and lacks the draw-backs associated therewith.

According to the invention, this object is achieved in the general sense, in that the cotton wool bud is provided on the end of a hollow rod which, with the insertion of a pressure-reducing and/or regulable shutoff valve, is connected to a sealed container which contains the refrigerant under the pressure of its own gas phase.

According to the invention, the refrigerant used is preferably a medium which is liquid even with a very low excess pressure and which is therefore kept in the liquid phase by its own gas phase without special cooling facilities, i.e. the major part of the volume of the reservoir contains liquid and a small quantity of gas, the liquid phase reducing to the extent that use occurs and the volume released being filled up by the gas phase. The outward flow takes place via the cotton wool bud on operating the valve. In this manner, the effect is obtained that refrigerants which have a boiling point is lower than 0° C. rapidly being about cell freezing as a result of further pressure reduction in the cotton wool bud and as a result of the large internal surface of the cotton woold bud which cause a lower temperature (measured at the cotton wool bud) than the boiling point of the refrigerant and are amply sufficient to bring about cell freezing in a short time.

Consideration must be given here to refrigerants which boil at a temperature situated between 0° C. and −50° C. In particular, these are refrigerants which boil between −0.5° C. and −43° C. As an example of a refrigerant with a boiling point of −0.5° C., mention may be made of n-butane; as an example of a refrigerant having a boiling point of approximately −43° C., mention may be made of propane.

Suitable refrigerants might be halogenated hydrocarbons, such as tetrafluoromethane, trifluoromethane, monochlorotrifluoromethane, hexafluoroethane, monobromotri fluoromethane, monochlorodifluoromethane, monochloropenta fluoroethane, dichlorodifluoromethane, 1,2-dichloro-, 1,1,2,2-tetrafluoroethane, trichloromonofluoromethane, 1,1,2-trichloro-, 1,2,2-trifluoroethane and 1,1-difluoro ethane, propane, n-butane, and isobutane. These are, however, often environmentally harmful. Dimethyl ether is to be preferred since it is environmentally acceptable.

The pressure of the gas phase is preferably kept below 5 bar, preferably even little more than atmospheric pressure.

With the method according to the invention it is therefore possible in a very simple manner and in a manner which can be immediately available to immediately generate very low temperatures which are considerably below the boiling point of the particular refrigerant itself.

The device for using the method can be implemented in various manners.

According to the invention, said device preferably consists of a spray can for accommodating the refrigerant, a pressure-reducing and shut-off valve to be operated with a finger on an end wall of the spray can with a supply tube extending into the liquid phase and a discharge tube, connecting to the discharge opening of the valve, on the end of which the cotton wool bud is situated. Spray cans are easily kept in stock without special facilities being necessary so that the practitioner can use the treatment at any instant and is no longer dependent on the delivery of a container filled with liquid nitrogen. This means an important reduction in costs and, consequently, also that the treatment can be carried out more easily and more cheaply.

Attention is drawn to the fact that spray cans containing a refrigerant are known per se, for example for use in electronics. Spray cans which deliver a jet of refrigerant are, however, less suitable for medical treatments since the jet is difficult to aim satisfactorily and the refrigerant splutters in all directions at the place to be treated, as a result of which unintended effects are obtained.

Preferably, the valve has a low flow rate capacity of not more than 60 ml/minute, preferably 30 ml/minute, so that when the knob of the valve is pressed in, a measured quantity of refrigerant can easily be released.

Attention is drawn to the fact that it is known from the laid-open Dutch patent application No. 7,308,008 that use is made of a liquid refrigerant with a low boiling point for carrying out cryosurgical treatments such as the removal of an eye lens affected by cataract in cataract operations making use of adhesion to the rod-shaped object which is brought to a low temperature by means of the refrigerant and which is brought into contact with the place to be treated, such as the eye lens. In this device, which is known per se and of small construction and which may be regarded as a throw-away article, the liquid refrigerant is also present in a container and flows out via a cotton wool plug on operating a valve. Said plug acts, however, as a means for the absorption of coolant liquid and not for the treatment. The refrigerant is used for cooling a rod which conducts heat rapidly and it is this rod which is used after cooling for carrying out the treatment. Said rod is situated at the end of the device facing away from the plug.

Furthermore, it is known from German Offenlegungsschrift No. 3,340,991 that dimethyl ether is used as propellent but also as solvent in spray cans for spraying-in of drugs to treat disorders of the air passages in the human or animal mouth, nose and throat cavity. This does not involve the freezing of cells but the application of a drug.

The invention will now be explained in more detail with reference to the drawing and with reference to examples.

The drawing shows a spray can 1 with an end wall 2 in which a pressure-reducing shut-off valve, not shown, and which is concealed from the eye by a covering cap 3 and can be operated if the covering cap is removed in a known manner and as is usual for spray cans. The spray can 1 contains a liquid refrigerant 4, the level of which is indicated at 5 and above which the gas phase 6 is situated. The valve extends into the liquid phase 4 of the refrigerant by means of a hose of flexible tubing 7. The debouchment of the valve contains a tube 8 into which a thinner tube 9 or narrow pipe is inserted and secured, the outlet opening of which is surrounded by a cotton wool plug 11.

On operating the valve, a quantity of liquid refrigerant flows via hose 7 and the valve through the tubes 8, 9 into the cotton wool plug 11, distributes itself there immediately over the large surface of the plug, vaporises and cools said cotton wool plug 11 to a very low temperature.

EXAMPLES

Mention is made below of a number of refrigerants, the latter being followed by their normal boiling point and the latter by the lowest temperature which it was possible to measure after 30 seconds at the cotton wool bud as a result of activating the expanding refrigerant.

| Refrigerant | Boiling point | Effective treatment temperature |
| --- | --- | --- |
| dimethyl ether | −24.8° C. | −45° C. |
| difluorodichloromethane | −29.8° C. | −48° C. |
| n-butane | −0.5° C. | −29° C. |
| isobutane | −11.7° C. | −35° C. |
| propane | −42.1° C. | −50° C. |

I claim:

1. In device for the therapeutic treatment of a portion of the skin of a human or animal by the freezing of said portion of said skin by application of a refrigerant thereto, said device comprising a spray can containing a liquid refrigerant that boils within the temperature range of 0° C. to −50° C., and a supply tube having a supply end positioned within said spray can and a discharge end having an outlet for said refrigerant, the improvement wherein said device further comprises a cotton wool bud encompassing said discharge end of said supply tube and which cotton wool bud surrounds said outlet of said supply tube and is permeable by said liquid refrigerant and has an exposed outer surface of cotton wool.

2. The device of claim 1 wherein said refrigerant boils at a temperature within the range of −0.5° C. and −43° C.

3. The device of claim 1 wherein said refrigerant is at a pressure of less than 5 bar within said spray can.

4. The device of claim 1 wherein said refrigerant comprises dimethyl ether.

* * * * *